(12) United States Patent
Kagan (10) Patent No.: US 8,603,074 B2
(45) Date of Patent: Dec. 10, 2013

(54) ABSORBABLE, REDUCED-PRESSURE MANIFOLDS AND SYSTEMS

(75) Inventor: Jonathan Kagan, Hopkins, MN (US)

(73) Assignee: KCI Licensing, Inc., San Antonio, TX (US)

( * ) Notice: Subject to any disclaimer, the term of this patent is extended or adjusted under 35 U.S.C. 154(b) by 1128 days.

(21) Appl. No.: 12/491,845

(22) Filed: Jun. 25, 2009

(65) Prior Publication Data

US 2009/0326515 A1    Dec. 31, 2009

Related U.S. Application Data

(60) Provisional application No. 61/075,699, filed on Jun. 25, 2008.

(51) Int. Cl.
*A61M 27/00* (2006.01)

(52) U.S. Cl.
USPC ............ 604/543; 604/313; 604/317; 604/541

(58) Field of Classification Search
USPC ............ 604/27, 28, 44, 48, 57, 73, 317, 540, 604/541, 543, 289, 290, 313; 602/43, 47, 602/53
See application file for complete search history.

(56) References Cited

U.S. PATENT DOCUMENTS

| | | |
|---|---|---|
| 1,355,846 A | 10/1920 | Rannells |
| 2,547,758 A | 4/1951 | Keeling |
| 2,632,443 A | 3/1953 | Lesher |
| 2,682,873 A | 7/1954 | Evans et al. |
| 2,910,763 A | 11/1959 | Lauterbach |
| 2,969,057 A | 1/1961 | Simmons |
| 3,066,672 A | 12/1962 | Crosby, Jr. et al. |
| 3,367,332 A | 2/1968 | Groves |
| 3,520,300 A | 7/1970 | Flower, Jr. |

(Continued)

FOREIGN PATENT DOCUMENTS

| | | |
|---|---|---|
| AU | 550575 A1 | 8/1982 |
| AU | 745271 | 4/1999 |

(Continued)

OTHER PUBLICATIONS

International Search Report and Written Opinion date mailed Apr. 12, 2010; PCT International Application No. PCT/US2009/048663.

(Continued)

*Primary Examiner* — Jacqueline Stephens
*Assistant Examiner* — Benedict L Hanrahan (57) ABSTRACT

A reduced-pressure treatment system includes an isolation device for isolating a tissue site from surrounding tissue for reduced-pressure treatment that is formed from a first material having a first bio-absorption term and at least a second material having a second and different bio-absorption term. The different materials allow the isolation device initially to function well for reduced-pressure treatment and then to experience degradation at a quicker pace which facilitates healing. In addition, a reduced-pressure manifold for treating a tissue site is presented that includes a flexible barrier member formed from a first material, which has a first bio-absorption term and formed with a first plurality of apertures; a second material, which has a second bio-absorption term, disposed within the plurality of apertures; wherein the first bio-absorption term is greater than the second bio-absorption term; and a reduced-pressure delivery member coupled to the barrier member for delivering reduced pressure to the second surface of the barrier member during reduced-pressure treatment.

15 Claims, 7 Drawing Sheets

(56) References Cited

U.S. PATENT DOCUMENTS

| | | |
|---|---|---|
| 3,568,675 A | 3/1971 | Harvey |
| 3,648,692 A | 3/1972 | Wheeler |
| 3,682,180 A | 8/1972 | McFarlane |
| 3,826,254 A | 7/1974 | Mellor |
| 3,833,002 A | 9/1974 | Palma |
| 4,080,970 A | 3/1978 | Miller |
| 4,096,853 A | 6/1978 | Weigand |
| 4,139,004 A | 2/1979 | Gonzalez, Jr. |
| 4,165,748 A | 8/1979 | Johnson |
| 4,184,510 A | 1/1980 | Murry et al. |
| 4,233,969 A | 11/1980 | Lock et al. |
| 4,245,630 A | 1/1981 | Lloyd et al. |
| 4,256,109 A | 3/1981 | Nichols |
| 4,261,363 A | 4/1981 | Russo |
| 4,275,721 A | 6/1981 | Olson |
| 4,284,079 A | 8/1981 | Adair |
| 4,297,995 A | 11/1981 | Golub |
| 4,333,468 A | 6/1982 | Geist |
| 4,373,519 A | 2/1983 | Errede et al. |
| 4,382,441 A | 5/1983 | Svedman |
| 4,392,853 A | 7/1983 | Muto |
| 4,392,858 A | 7/1983 | George et al. |
| 4,419,097 A | 12/1983 | Rowland |
| 4,465,485 A | 8/1984 | Kashmer et al. |
| 4,475,909 A | 10/1984 | Eisenberg |
| 4,480,638 A | 11/1984 | Schmid |
| 4,525,166 A | 6/1985 | Leclerc |
| 4,525,374 A | 6/1985 | Vaillancourt |
| 4,540,412 A | 9/1985 | Van Overloop |
| 4,543,100 A | 9/1985 | Brodsky |
| 4,548,202 A | 10/1985 | Duncan |
| 4,551,139 A | 11/1985 | Plaas et al. |
| 4,569,348 A | 2/1986 | Hasslinger |
| 4,605,399 A | 8/1986 | Weston et al. |
| 4,608,041 A | 8/1986 | Nielsen |
| 4,640,688 A | 2/1987 | Hauser |
| 4,655,754 A | 4/1987 | Richmond et al. |
| 4,664,662 A | 5/1987 | Webster |
| 4,699,792 A * | 10/1987 | Nick et al. ............... 424/446 |
| 4,710,165 A | 12/1987 | McNeil et al. |
| 4,733,659 A | 3/1988 | Edenbaum et al. |
| 4,743,232 A | 5/1988 | Kruger |
| 4,758,220 A | 7/1988 | Sundblom et al. |
| 4,787,888 A | 11/1988 | Fox |
| 4,826,494 A | 5/1989 | Richmond et al. |
| 4,838,883 A | 6/1989 | Matsuura |
| 4,840,187 A | 6/1989 | Brazier |
| 4,863,449 A | 9/1989 | Therriault et al. |
| 4,872,450 A | 10/1989 | Austad |
| 4,878,901 A | 11/1989 | Sachse |
| 4,897,081 A | 1/1990 | Poirier et al. |
| 4,906,233 A | 3/1990 | Moriuchi et al. |
| 4,906,240 A | 3/1990 | Reed et al. |
| 4,919,654 A | 4/1990 | Kalt et al. |
| 4,941,882 A | 7/1990 | Ward et al. |
| 4,953,565 A | 9/1990 | Tachibana et al. |
| 4,969,880 A | 11/1990 | Zamierowski |
| 4,985,019 A * | 1/1991 | Michelson ............... 604/180 |
| 5,034,006 A * | 7/1991 | Hosoda et al. ............ 604/317 |
| 5,037,397 A | 8/1991 | Kalt et al. |
| 5,086,170 A | 2/1992 | Luheshi et al. |
| 5,092,858 A | 3/1992 | Benson et al. |
| 5,100,396 A | 3/1992 | Zamierowski |
| 5,134,994 A | 8/1992 | Say |
| 5,149,331 A | 9/1992 | Ferdman et al. |
| 5,167,613 A | 12/1992 | Karami et al. |
| 5,176,663 A | 1/1993 | Svedman et al. |
| 5,215,522 A | 6/1993 | Page et al. |
| 5,232,453 A | 8/1993 | Plass et al. |
| 5,261,893 A | 11/1993 | Zamierowski |
| 5,278,100 A | 1/1994 | Doan et al. |
| 5,279,550 A | 1/1994 | Habib et al. |
| 5,298,015 A | 3/1994 | Komatsuzaki et al. |
| 5,342,376 A | 8/1994 | Ruff |
| 5,344,415 A | 9/1994 | DeBusk et al. |
| 5,358,494 A | 10/1994 | Svedman |
| 5,437,622 A | 8/1995 | Carion |
| 5,437,651 A | 8/1995 | Todd et al. |
| 5,466,462 A | 11/1995 | Rosenthal et al. |
| 5,527,293 A | 6/1996 | Zamierowski |
| 5,549,584 A | 8/1996 | Gross |
| 5,556,375 A | 9/1996 | Ewall |
| 5,607,388 A | 3/1997 | Ewall |
| 5,636,643 A | 6/1997 | Argenta et al. |
| 5,645,081 A | 7/1997 | Argenta et al. |
| 6,071,267 A | 6/2000 | Zamierowski |
| 6,135,116 A | 10/2000 | Vogel et al. |
| 6,241,747 B1 | 6/2001 | Ruff |
| 6,287,316 B1 | 9/2001 | Agarwal et al. |
| 6,345,623 B1 | 2/2002 | Heaton et al. |
| 6,488,643 B1 | 12/2002 | Tumey et al. |
| 6,493,568 B1 | 12/2002 | Bell et al. |
| 6,553,998 B2 | 4/2003 | Heaton et al. |
| 6,814,079 B2 | 11/2004 | Heaton et al. |
| 7,951,124 B2 * | 5/2011 | Boehringer et al. .......... 604/319 |
| 2002/0077261 A1 | 6/2002 | Saadat |
| 2002/0115951 A1 | 8/2002 | Norstrem et al. |
| 2002/0120185 A1 | 8/2002 | Johnson |
| 2002/0143286 A1 | 10/2002 | Tumey |
| 2005/0228505 A1 | 10/2005 | Cornet et al. |
| 2007/0032763 A1 | 2/2007 | Vogel |
| 2007/0185426 A1 | 8/2007 | Ambrosio et al. |
| 2008/0275409 A1 | 11/2008 | Kane et al. |

FOREIGN PATENT DOCUMENTS

| | | |
|---|---|---|
| AU | 755496 | 2/2002 |
| CA | 2005436 | 6/1990 |
| DE | 26 40 413 A1 | 3/1978 |
| DE | 43 06 478 A1 | 9/1994 |
| DE | 295 04 378 U1 | 10/1995 |
| EP | 0100148 A1 | 2/1984 |
| EP | 0117632 A2 | 9/1984 |
| EP | 0161865 A2 | 11/1985 |
| EP | 0358302 A2 | 3/1990 |
| EP | 0 562 864 A1 | 9/1993 |
| EP | 1018967 B1 | 8/2004 |
| GB | 692578 | 6/1953 |
| GB | 2 195 255 A | 4/1988 |
| GB | 2 197 789 A | 6/1988 |
| GB | 2 220 357 A | 1/1990 |
| GB | 2 235 877 A | 3/1991 |
| GB | 2 333 965 A | 8/1999 |
| GB | 2 329 127 B | 8/2000 |
| JP | 4129536 | 4/1992 |
| SG | 71559 | 4/2002 |
| WO | WO 80/02182 | 10/1980 |
| WO | WO 87/04626 | 8/1987 |
| WO | WO 90/10424 | 9/1990 |
| WO | WO 93/09727 | 5/1993 |
| WO | WO 94/20041 | 9/1994 |
| WO | WO 96/05873 | 2/1996 |
| WO | WO 97/18007 | 5/1997 |
| WO | WO 99/13793 | 3/1999 |
| WO | WO 02/092783 A2 | 11/2002 |
| WO | WO 2007/106592 A2 | 9/2007 |

OTHER PUBLICATIONS

N.A. Bagautdinov, "Variant of External Vacuum Aspiration in the Treatment of Purulent Diseases of the Soft Tissues," *Current Problems in Modern Clinical Surgery: Interdepartmental Collection*, edited by V. Ye Volkov et al. (Chuvashia State University, Cheboksary, U.S.S.R. 1986);pp. 94-96 (certified translation).

Louis C. Argenta, MD and Michael J. Morykwas, PhD; "Vacuum-Assisted Closure: A New Method for Wound Control and Treatment: Clinical Experience"; Annals of Plastic Surgery, vol. 38, No. 6, Jun. 1997; pp. 563-576.

Susan Mendez-Eastmen, RN; "When Wounds Won't Heal" RN Jan. 1998, vol. 61 (1); Medical Economics Company, Inc., Montvale, NJ, USA; pp. 20-24.

(56) References Cited

OTHER PUBLICATIONS

James H. Blackburn, II, MD, et al; "Negative-Pressure Dressings as a Bolster for Skin Grafts"; Annals of Plastic Surgery, vol. 40, No. 5, May 1998, pp. 453-457.
John Masters; "Reliable, Inexpensive and Simple Suction Dressings"; Letter to the Editor, British Journal of Plastic Surgery, 1998, vol. 51 (3), p. 267; Elsevier Science/The British Association of Plastic Surgeons, UK.
S.E. Greer, et al "The Use of Subatmospheric Pressure Dressing Therapy to Close Lymphocutaneous Fistulas of the Groin" British Journal of Plastic Surgery (2000), 53, pp. 484-487.
George V. Letsou, MD., et al; "Stimulation of Adenylate Cyclase Activity in Cultured Endothelial Cells Subjected to Cyclic Stretch"; Journal of Cardiovascular Surgery, 31, 1990, pp. 634-639.
Orringer, Jay, et al; "Management of Wounds in Patients with Complex Enterocutaneous Fistulas"; Surgery, Gynecology & Obstetrics, Jul. 1987, vol. 165, pp. 79-80.
International Search Report for PCT International Application PCT/GB95/01983; Nov. 23, 1995.
PCT International Search Report for PCT International Application PCT/GB98/02713; Jan. 8, 1999.
PCT Written Opinion; PCT International Application PCT/GB98/02713; Jun. 8, 1999.
PCT International Examination and Search Report, PCT International Application PCT/GB96/02802; Jan. 15, 1998 & Apr. 29, 1997.
PCT Written Opinion, PCT International Application PCT/GB96/02802; Sep. 3, 1997.
Dattilo, Philip P., Jr., et al; "Medical Textiles: Application of an Absorbable Barbed Bi-directional Surgical Suture"; Journal of Textile and Apparel, Technology and Management, vol. 2, Issue 2, Spring 2002, pp. 1-5.
Kostyuchenok, B.M., et al; "Vacuum Treatment in the Surgical Management of Purulent Wounds"; Vestnik Khirurgi, Sep. 1986, pp. 18-21 and 6 page English translation thereof.
Davydov, Yu. A., et al; "Vacuum Therapy in the Treatment of Purulent Lactation Mastitis"; Vestnik Khirurgi, May 14, 1986, pp. 66-70, and 9 page English translation thereof.
Yusupov. Yu. N., et al; "Active Wound Drainage", Vestnik Khirurgi, vol. 138, Issue 4, 1987, and 7 page English translation thereof.
Davydov, Yu. A., et al; "Bacteriological and Cytological Assessment of Vacuum Therapy for Purulent Wounds"; Vestnik Khirurgi, Oct. 1988, pp. 48-52, and 8 page English translation thereof.
Davydov, Yu. A., et al; "Concepts for the Clinical-Biological Management of the Wound Process in the Treatment of Purulent Wounds by Means of Vacuum Therapy"; Vestnik Khirurgi, Jul. 7, 1980, pp. 132-136, and 8 page English translation thereof.
Chariker, Mark E., M.D., et al; "Effective Management of incisional and cutaneous fistulae with closed suction wound drainage"; Contemporary Surgery, vol. 34, Jun. 1989, pp. 59-63.
Egnell Minor, Instruction Book, First Edition, 300 7502, Feb. 1975, pp. 24.
Egnell Minor: Addition to the Users Manual Concerning Overflow Protection—Concerns all Egnell Pumps, Feb. 3, 1983, pp. 2.
Svedman, P.: "Irrigation Treatment of Leg Ulcers", The Lancet, Sep. 3, 1983, pp. 532-534.
Chinn, Steven D. et al.: "Closed Wound Suction Drainage", The Journal of Foot Surgery, vol. 24, No. 1, 1985, pp. 76-81.
Arnljots, Björn et al.: "Irrigation Treatment in Split-Thickness Skin Grafting of Intractable Leg Ulcers", Scand J. Plast Reconstr. Surg., No. 19, 1985, pp. 211-213.
Svedman, P.: "A Dressing Allowing Continuous Treatment of a Biosurface", IRCS Medical Science: Biomedical Technology, Clinical Medicine, Surgery and Transplantation, vol. 7, 1979, p. 221.
Svedman, P. et al.: "A Dressing System Providing Fluid Supply and Suction Drainage Used for Continuous or Intermittent Irrigation", Annals of Plastic Surgery, vol. 17, No. 2, Aug. 1986, pp. 125-133.
K.F. Jeter, T.E. Tintle, and M. Chariker, "Managing Draining Wounds and Fistulae: New and Established Methods," Chronic Wound Care, edited by D. Krasner (Health Management Publications, Inc., King of Prussia, PA 1990), pp. 240-246.
G. Živadinović, V. Đukić, Ž. Maksimović, Đ. . Radak, and P. Peška, "Vacuum Therapy in the Treatment of Peripheral Blood Vessels," Timok Medical Journal 11 (1986), pp. 161-164 (certified translation).
F.E. Johnson, "An Improved Technique for Skin Graft Placement Using a Suction Drain," Surgery, Gynecology, and Obstetrics 159 (1984), pp. 584-585.
A.A. Safronov, Dissertation Abstract, Vacuum Therapy of Trophic Ulcers of the Lower Leg with Simultaneous Autoplasty of the Skin (Central Scientific Research Institute of Traumatology and Orthopedics, Moscow, U.S.S.R. 1967) (certified translation).
M. Schein, R. Saadia, J.R. Jamieson, and G.A.G. Decker, "The 'Sandwich Technique' in the Management of the Open Abdomen," British Journal of Surgery 73 (1986), pp. 369-370.
D.E. Tribble, An Improved Sump Drain-Irrigation Device of Simple Construction, Archives of Surgery 105 (1972) pp. 511-513.
M.J. Morykwas, L.C. Argenta, E.I. Shelton-Brown, and W. McGuirt, "Vacuum-Assisted Closure: A New Method for Wound Control and Treatment: Animal Studies and Basic Foundation," Annals of Plastic Surgery 38 (1997), pp. 553-562 (Morykwas I).
C.E. Tennants, "The Use of Hypermia in the Postoperative Treatment of Lesions of the Extremities and Thorax," Journal of the American Medical Association 64 (1915), pp. 1548-1549.
Selections from W. Meyer and V. Schmieden, Bier's Hyperemic Treatment in Surgery, Medicine, and the Specialties: A Manual of Its Practical Application, (W.B. Saunders Co., Philadelphia, PA 1909), pp. 17-25, 44-64, 90-96, 167-170, and 210-211.
V.A. Solovev et al., Guidelines, The Method of Treatment of Immature External Fistulas in the Upper Gastrointestinal Tract, editor-in-chief Prov. V.I. Parahonyak (S.M. Kirov Gorky State Medical Institute, Gorky, U.S.S.R. 1987) ("Solovev Guidelines").
V.A. Kuznetsov & N.A. Bagautdinov, "Vacuum and Vacuum-Sorption Treatment of Open Septic Wounds," in II All-Union Conference on Wounds and Wound Infections: Presentation Abstracts, edited by B.M. Kostyuchenok et al. (Moscow, U.S.S.R. Oct. 28-29, 1986) pp. 91-92 ("Bagautdinov II").
V.A. Solovev, Dissertation Abstract, Treatment and Prevention of Suture Failures after Gastric Resection (S.M. Kirov Gorky State Medical Institute, Gorky, U.S.S.R. 1988) ("Solovev Abstract").
Partial Search Report date mailed Dec. 4, 2009; PCT International Application No. PCT/US2009/048663.

\* cited by examiner

ABSORBABLE, REDUCED-PRESSURE MANIFOLDS AND SYSTEMS

CROSS-REFERENCE TO RELATED APPLICATIONS

This application claims the benefit, under 35 U.S.C. §119(e), of the filing of U.S. Provisional Patent Application Ser. No. 61/075,699, entitled "Absorbable, Reduced-Pressure Manifold and System," filed Jun. 25, 2008, and that application is incorporated herein by reference for all purposes.

BACKGROUND

The present invention relates generally to medical treatment systems and in particular to absorbable, reduced-pressure manifolds and systems.

Clinical studies and practice have shown that providing reduced pressure in proximity to a tissue site augments or accelerates the growth of new tissue at the tissue site. The applications of this phenomenon are numerous, but application of reduced pressure has been particularly successful in treating wounds. This treatment (frequently referred to in the medical community as "negative pressure wound therapy," "reduced pressure therapy," or "vacuum therapy") provides a number of benefits, including faster healing and increased formulation of granulation tissue. Typically, reduced pressure is applied to the tissue through a porous pad or other manifold device. The porous pad contains cells or pores that are capable of distributing reduced pressure to the tissue and channeling fluids that are drawn from the tissue. The porous pad may be incorporated into a dressing having other components that facilitate treatment. Reduced pressure therapy also has been applied to treat subcutaneous wounds and to promote bone regeneration.

SUMMARY

Shortcomings with certain aspects of reduced-pressure treatment systems are addressed by the present invention as shown and described in a variety of illustrative embodiments herein. According to an illustrative embodiment, a reduced-pressure manifold for treating a tissue site includes a barrier member formed from a first bioabsorbable material and having a first surface and a second, tissue-facing surface. The barrier member is formed with a first plurality of apertures. The first material has a first bio-absorption term ($BA_1$). A second bioabsorbable material is disposed within the plurality of apertures and is operable to form a temporary seal. The second material has a second bio-absorption term ($BA_2$). The first bio-absorption term is different than the second bio-absorption term ($BA_1 \neq BA_2$). The reduced-pressure manifold may also include a reduced-pressure delivery member coupled to the barrier member for delivering reduced pressure to the second surface of the barrier member during treatment.

According to another illustrative embodiment, a reduced-pressure pressure delivery system for percutaneous delivery of reduced pressure to a tissue site includes a reduced-pressure manifold formed from a first material having a first bio-absorption term and a second material having second bio-absorption term. The reduced-pressure manifold has an insertion position and an activation position. The system further includes a reduced-pressure delivery member having a distal end with at least one delivery aperture for delivering reduced pressure to the tissue site and an insertion device for percutaneously delivering the reduced-pressure manifold and the distal end of the reduced-pressure delivery tube to the tissue site and transitioning the reduced-pressure manifold from the insertion position to the activation position. The first bio-absorption term may be greater than the second bio-absorption term.

According to another illustrative embodiment, a reduced-pressure treatment system includes an isolation device for isolating a tissue site from surrounding tissue for reduced-pressure treatment. The isolation device includes a first material having a bio-absorption term ($BA_1$) and a second material having a second and different bio-absorption term ($BA_2$). The system further includes a reduced-pressure source for providing a reduced pressure and a reduced-pressure delivery conduit fluidly coupling the isolation device and the reduced-pressure source.

According to another illustrative embodiment, a method of manufacturing a reduced-pressure manifold includes the steps of: forming a flexible barrier member from a first material having a first bio-absorption term ($BA_1$). The flexible barrier member has a first surface and a second, tissue-facing surface. The method further includes forming a first plurality of apertures in the barrier member and disposing a second material in the first plurality of apertures. The second material has a second bio-absorption term ($BA_2$). The first bio-absorption term is different than the second bio-absorption term ($BA_1 \neq BA_2$).

According to another illustrative embodiment, a method for treating a tissue site with reduced pressure includes the step of using a reduced-pressure delivery member to deploy a reduced-pressure manifold proximate the tissue site. The reduced-pressure manifold includes a barrier member formed from a first material, which has a first bio-absorption term ($BA_1$), and having a first surface and a second, tissue-facing surface. The barrier member is formed with a first plurality of apertures. The apertures have a second material disposed within the plurality of apertures whereby a temporary seal is formed. The second material has a second bio-absorption term ($BA_2$). The first bio-absorption term is different from the second bio-absorption term ($BA_1 \neq BA_2$). The method further includes coupling a reduced-pressure delivery member to the barrier member for delivering reduced pressure to the second surface of the barrier member during treatment. The method further includes providing reduced-pressure to the reduced-pressure manifold; removing the reduced-pressure delivery member; and allowing the reduced-pressure manifold to absorb.

According to another illustrative embodiment, a reduced-pressure manifold for treating a tissue site includes a barrier member formed from a material and having a first surface and a second, tissue-facing surface and wherein the barrier member is formed with a first plurality of material portions having a first thickness ($t_1$) and a second plurality of material portions having a second thickness ($t_2$). The first thickness ($t_1$) is greater than the second thickness ($t_2$). An effective bio-absorption term of the first plurality of material portions is greater than an effective bio-absorption term of the second plurality of material portions. The manifold may further include a reduced-pressure delivery member coupled to the barrier member for delivering reduced pressure to the second surface of the barrier member during treatment.

Other features and advantages of the illustrative embodiments will become apparent with reference to the drawings and detailed description that follow.

DETAILED DESCRIPTION

In the following detailed description of the illustrative embodiments, reference is made to the accompanying drawings that form a part hereof. These embodiments are described in sufficient detail to enable those skilled in the art to practice the invention, and it is understood that other embodiments may be utilized and that logical structural, mechanical, electrical, and chemical changes may be made without departing from the spirit or scope of the invention. To avoid detail not necessary to enable those skilled in the art to practice the embodiments described herein, the description may omit certain information known to those skilled in the art. The following detailed description is, therefore, not to be taken in a limiting sense, and the scope of the illustrative embodiments are defined only by the appended claims.

Figure 1:
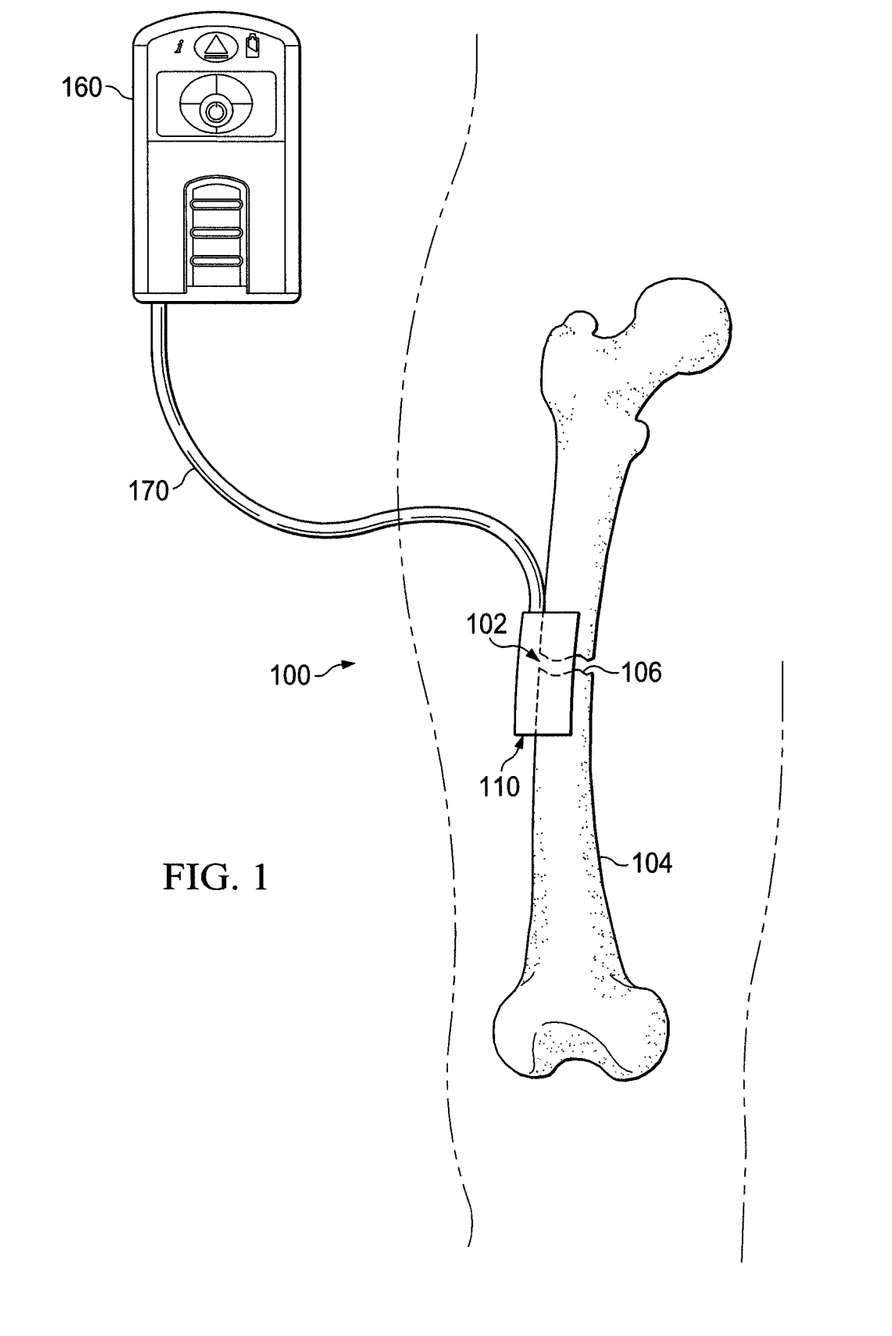
FIG. 1 is a schematic, perspective view of an illustrative embodiment of a system for delivering reduced-pressure to a tissue site.

Referring to FIG. 1, an illustrative reduced-pressure delivery system 100 is shown treating a tissue site 102, which in this illustration is a bone 104. When used to promote bone tissue growth, reduced pressure tissue treatments may increase the rate of healing associated with a fracture, a non-union, a void, or other bone defect; help improve recovery from osteomyelitis; increase localized bone densities in patients suffering from osteoporosis; or speed and improve oseointegration of orthopedic implants such as hip implants, knee implants, and fixation devices. As used herein, "or" does not require mutual exclusivity. The reduced-pressure delivery system 100 may be used on these tissue types and sites as well as others. In this illustrative embodiment, the reduced-pressure delivery system 100 is shown treating a bone fracture 106.

The reduced-pressure delivery system 100 includes a reduced-pressure source 160 that may take many different embodiments. The reduced-pressure source 160 provides reduced pressure as a part of the reduced-pressure delivery system 100. The term "reduced pressure" as used herein generally refers to a pressure less than the ambient pressure at a tissue site that is being subjected to treatment. In most cases, this reduced pressure will be less than the atmospheric pressure at which the patient is located. Alternatively, the reduced pressure may be less than a hydrostatic pressure of tissue at the tissue site. Although the terms "vacuum" and "negative pressure" may be used to describe the pressure applied to the tissue site, the actual pressure applied to the tissue site may be significantly more than the pressure normally associated with a complete vacuum. Unless otherwise indicated, values of pressure stated herein are gauge pressures.

The reduced pressure delivered by the reduced-pressure source 160 may be constant or varied (patterned or random) and may be delivered continuously or intermittently. In order to maximize patient mobility and ease, the reduced-pressure source 160 may be a battery-powered, reduced-pressure generator. This facilitates application in the operating room and provides mobility and convenience for the patient during the rehabilitation phase. Other sources of reduced pressure might be utilized such as V.A.C.® therapy unit, which is available from KCI of San Antonio, Tex., wall suction, or a mechanical unit.

The reduced pressure developed by the reduced-pressure source 160 is delivered through a reduced-pressure delivery conduit 170, or medical conduit or tubing, to a reduced-pressure manifold 110. An interposed hydrophobic membrane filter may be interspersed between the reduced-pressure conduit 170 and the reduced-pressure source 160. The reduced-pressure manifold 110 may be surgically or percutaneously inserted into the patient and placed proximate the bone fracture 106. When percutaneously inserted, the reduced-pressure delivery conduit 170 may be inserted through a sterile insertion sheath that penetrates the epidermis of the patient. The reduced-pressure manifold 110 includes at least two materials having different absorption terms.

Figure 2:
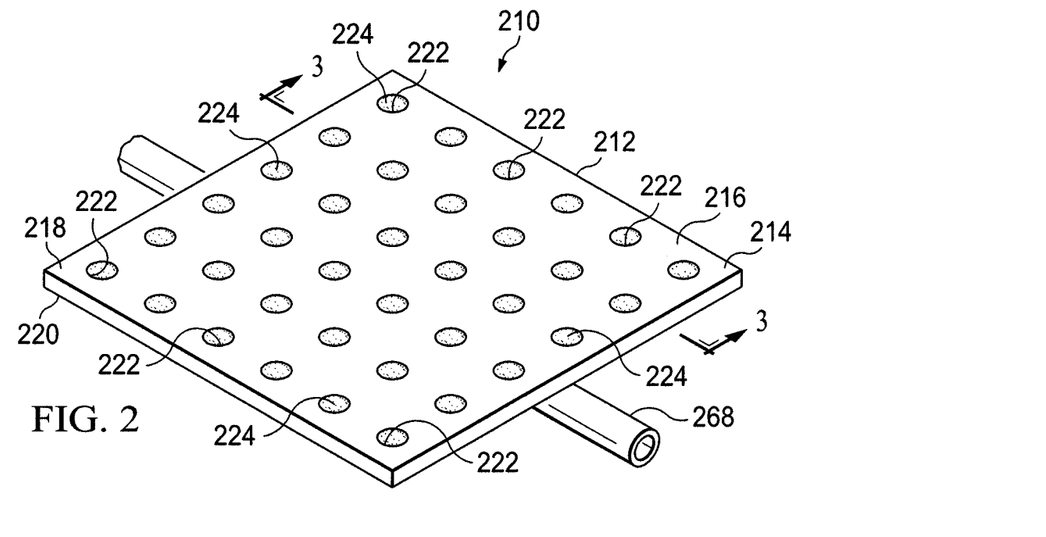
FIG. 2 is a schematic, perspective view of an illustrative embodiment of a reduced-pressure manifold.
Figure 3:
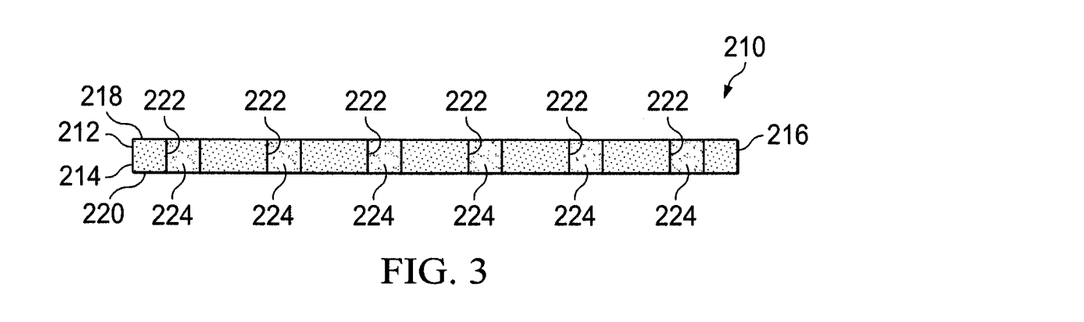
FIG. 3 is a schematic cross-section of the reduced-pressure manifold of FIG. 2.

Referring now primarily to FIGS. 2 and 3, an illustrative embodiment of a reduced-pressure manifold 210 is presented. The reduced-pressure manifold 210 includes a barrier member 212 that is formed as a barrier body 214 from a first material 216, which may be rigid or flexible. The reduced-pressure manifold member 210 may function as an isolation device that includes a flexible barrier member for maintaining reduced pressure proximate the tissue site.

The barrier body 214 of the barrier member 212 has a first surface 218 and a second, treatment-facing (or tissue-facing) surface 220. A first plurality of apertures 222 is formed in the barrier body 214. The apertures 222 may be filled with a second material 224. The apertures 222 may completely cover the barrier body 214 as shown in FIG. 2 or may partially cover the barrier body 214. The apertures 222 may be randomly applied or applied in various patterns such as the uniform pattern shown in FIG. 2. The barrier body 214 is presented as a plane of material, but it could also be formed into various shapes and contours for application to different tissue sites.

During treatment, the barrier body 214 helps apply reduced pressure to the tissue site and to prevent ingress of potentially interfering tissue during the treatment phase. Once treatment is completed it may be desirable for the treated tissue to be in chemical communication with other tissues that were previously subjected to the barrier body 214. The inclusion of additional materials that absorb relatively quickly in the reduced-pressure manifold 210 helps speed this communication. The relative absorption rates of the materials and other design features may be controlled to achieve various effects.

In choosing the first material 216 and second material 224, a number of design parameters may be considered. The first material 216 may be selected to provide mechanical properties such as strength in order to provide the necessary structure for the reduced-pressure treatment using the reduced-pressure manifold 210. At the same time, once treatment is complete, it may be desirable for the reduced-pressure manifold 210 to be absorbed and degrade as quickly as possible or at least to begin the chemical communication of the treatment tissue with other surrounding tissues that were previously subjected to the barrier member 212 of the reduced-pressure manifold 210. This latter consideration may be controlled by a number of design parameters such as the absorption rate or absorption term of the second material 224, the diameter of the apertures 222, the thickness of barrier body 214, etc. For example, a small diameter aperture in a thick body 214 will have less mechanical impact and a slower degradation than a larger diameter pore in a thin body 214. In other situations, lasting mechanical strength may be desirous and maintenance of portions of the manifold 210, e.g., the portions composed of material 216, as a tissue stabilizing element may be achieved by tissue growing through the apertures 222. In this case the first absorption rate $BA_1$ (see below) may be selected for a clinically relevant duration and $BA_2$ may selected to absorb faster to enable trans-aperture tissue growth.

The first material 216 has a given absorption rate that results in a first bio-absorption term ($BA_1$), and the second material 224 has a given absorption rate that results in a second bio-absorption term ($BA_2$). Numerous materials may be used for materials 216 and 224. For example, the first material 216 may be a polyglycolic acid material with an absorption time or term ($BA_1$) of several months, and the second material 224 may be a dried gelatinous material having an absorption time or term ($BA_2$) of only several days or less. Other suitable bio-absorbable materials may include, without limitation, a polymeric blend of polylactic acid (PLA) and polyglycolic acid (PGA). The polymeric blend may also include without limitation polycarbonates, polyfumarates, and capralactones. Either the first material 216, the second material 224, or both may be a porous material having interconnected cells that permit fluid flow through the material, or the materials may be impervious to fluids.

The absorption terms of the materials may be chosen in different combinations for different purposes. If the first material is a polyglycolic acid material and the second material is dried gelatinous material, then the first bio-absorption term ($BA_1$) will be greater than the second bio-absorption term ($BA_2$), i.e., $BA_1 > BA_2$. In other embodiments, the materials may be selected the other way, i.e., $BA_2 > BA_1$. The first material 216 and second material 224 may also be covered by a third material that reduces the rate of degradation of the second material 224 as another control mechanism.

The absorption of one of the materials, e.g., the second material 224, may open up pore sizes, or apertures 222, that are adequate to achieve a desired purpose. For example, in one illustrative embodiment, the pore size may be large enough to allow chemical signaling, but small enough to restrict cell migration. In a more specific example, with some tissues, a pore size of about 50 microns would prevent cell migration for the tissues involved, but would allow chemical signaling. The pore actual size desired would vary some depending on the tissues involved. Alternatively, the pore size may intentionally be sized to allow cell migration or trans-aperture growth after one of the materials is absorbed. A third material may be added to allow for delivery of a medicine or other substances and may be designed to become available only after one of the other two materials is absorbed or some portion thereof.

Numerous combinations are possible to accommodate different situations. A few examples follow. In the first illustrative example, the first bio-absorption term ($BA_1$) is at least one month and the second bio-absorption term ($BA_2$) is less than one week under typical conditions for the deployed reduced-pressure manifold 210. In another illustrative example, the first bio-absorption term ($BA_1$) is at least one week and the second bio-absorption term ($BA_2$) is less than three days. In a third illustrative example, the first bio-absorption term ($BA_1$) is at least two days and the second bio-absorption term ($BA_2$) is less than one day. In still another illustrative example, the first bio-absorption term ($BA_1$) is on the order of about 90 days and the second bio-absorption term ($BA_2$) is on the order of about 10-14 days. In still another illustrative example, the first bio-absorption term ($BA_1$) is longer than 90 days and the second bio-absorption term ($BA_2$) is shorter than 10 days. In some situations, the first bio-absorption term ($BA_1$) may be on the order of years or even decades. Again, numerous possibilities exist and moreover a third material may be included and other parameters, such as the thicknesses, may be varied as well. If a third material is added, the third material may be in the form of deposits, e.g., balls, of a third material, formed within the first material 216 to make the first material 216 more porous once the third material is absorbed or disposed in apertures (see FIG. 4).

The ratio of the thickness of the first material 216 to the diameter or width of the apertures 222 may be selected to control or adjust the bio-absorption properties of the manifold 210. For example, an aperture having a small diameter in a relatively thick sheet would have less mechanical impact and a slower absorption rate than a large diameter aperture in a thinner sheet. The first material 216 and the second material 224 may optionally be coated with other materials that may retard the absorption of the first material 216, the second material 224, or both.

In another illustrative embodiment, the materials may be selected such that $BA_2$ is greater than $BA_1$ (i.e., $BA_2 > BA_1$). In that situation, the distributed second material that remains after the first material is absorbed will not typically resist motion of the tissue or offer mechanical functionality to the area. Many other combinations are possible with respect to the materials and parameters mentioned.

The manifold body 214 is schematically shown in the illustrative embodiment of FIG. 2 as a planar, thin member, but a non-planar member, e.g., a thicker member or varied shape member, may be used as the thicker member may be advantageous in some clinical situations. Moreover, as noted, variations on the apertures and materials (see, e.g., FIGS. 3, 4, 5, 6, and 7) may be used to construct the reduced-pressure manifold 210, or barrier, with differential absorption characteristics. For a more specific illustrative example, a reduced-pressure manifold 210 may be formed from a first material (with $BA_1$) of polyglycolic acid (PGA) formed into a felted mat, such a felted mat is available from Biomedical Structures, LLC of Warwick, R.I., and from a second material of a dried gelatinous material ($BA_2$). In this illustration, $BA_1 > BA_2$. The gelatin could be dried in place after being applied onto and into the felt when in a liquid state. In this case, bio-absorption of the second material would allow tissue in growth into the open area within the felt. The felted PGA would then remain in place for a period of time as a mechanical support structure. Still another illustrative embodiment could use an open-cell PGA foam in place of the felt described in the previous example. Again, many other permutations are possible.

Referring still to FIG. 2, the reduced-pressure delivery member 268, or reduced-pressure delivery conduit, is associated with the reduced-pressure manifold 210. The reduced-pressure delivery member 268 delivers reduced pressure to the tissue site, proximate the manifold 210, and is thus shown on the second, tissue-facing surface 220 of the reduced-pressure manifold 210 to allow reduced pressure to be developed between the barrier member 212 and the tissue to be treated. The reduced-pressure delivery member 268 may have delivery apertures (not shown) formed on a portion or have a shaped distal end to facilitate delivery of the reduced pressure. The reduced-pressure delivery member 268 may include multiple lumens, for example the reduced-pressure delivery member 268 could be a dual lumen member with one lumen delivering a substance such as a fluid to the tissue site and the other lumen delivering reduced pressure and removing fluids. Once treatment is complete, the reduced-pressure delivery member 268 may be removed from the patient's body, but the reduced-pressure manifold 210 may be left in place for subsequent absorption.

Figure 4:
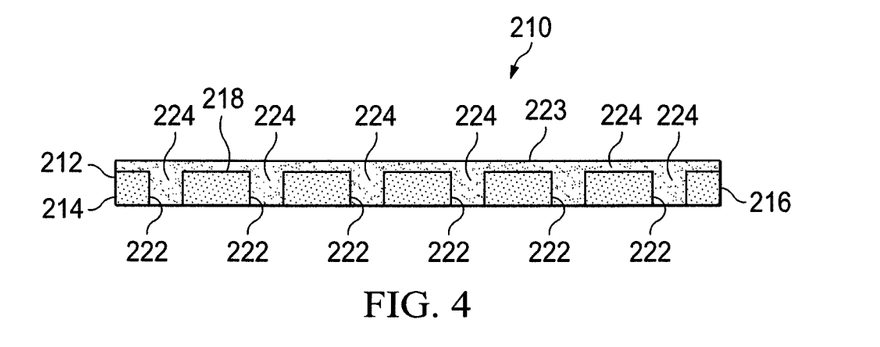
FIG. 4 is a schematic cross-section of another illustrative reduced-pressure manifold.

Referring now primarily to FIG. 4, an alternative embodiment of the reduced-pressure manifold 210 is presented. The barrier member 212, which is formed from the first material 216, has the plurality of apertures 222 filled with the second material 224. In addition, however, the second material 224 also forms an overlay 223 by overlaying the apertures 222 and the first surface 218 of the barrier body 214. The second material 224 may be applied by coating the first surface 218 and filling the apertures 222.

Figure 5:
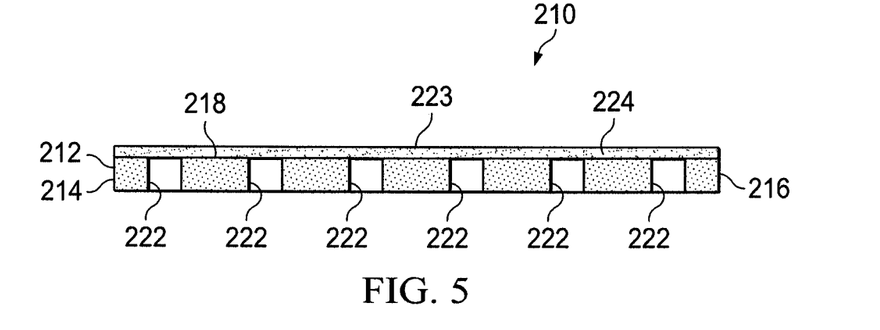
FIG. 5 is a schematic cross-section of another illustrative reduced-pressure manifold.

Referring now primarily to FIG. 5, another alternative embodiment of the reduced-pressure manifold 210 is presented. The barrier member 212, which is formed from the first material 216, has the plurality of apertures 222. In addition, however, in this illustrative embodiment, the apertures 222 are not filled and the second material 224 forms the overlay 223 by overlaying (but not filling) the apertures 222 and the first surface 218 of the barrier body 214. The second material 224 may be applied by laminating the first surface 218. In still another alternative embodiment (not shown), the apertures 222 may be filled with the second material 224 and a third material may be used to form an overlay 223.

Figure 6:
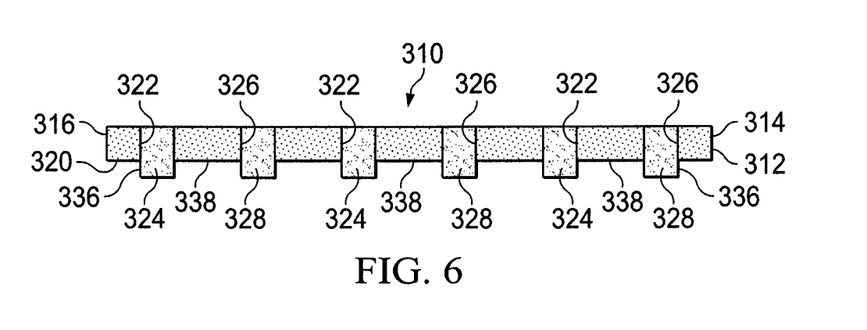
FIG. 6 is a schematic cross-section of another illustrative reduced-pressure manifold.

Referring now to FIG. 6, another illustrative embodiment of a reduced-pressure manifold 310 is presented. The reduced-pressure manifold 310 is analogous is many respects to the reduced-pressure manifold 210 of FIG. 3, but a second material 324 is disposed in a plurality of apertures 322 to an extent that the second material extends beyond a second surface 320 to form a plurality of projections 336. The reduced-pressure manifold 310 has a barrier member 312 having a barrier body 314 formed from a first material 316. The barrier body 314 is formed with the plurality of apertures 322.

The projections 336 that extend from the apertures 322 form flow channels 338 between the projections 336. The flow channels 338 may be particularly advantageous if the first material 316 and the second material 324 are impervious to fluids. Variations in the size, shape, and spacing of the projections 336 may be used to alter the size and flow characteristics of the flow channels 338. The barrier body 314 may be formed with a second plurality of apertures 326 through the barrier body 314 that may have a third material 328 disposed in the apertures 326. The third material has a bio-absorption term ($BA_3$) that may be varied for further performance and control of the degradation, or absorption, pattern of the reduced-pressure manifold 310.

In the embodiments, herein the plurality of apertures (e.g., 322 and 326 of FIG. 6) may be over the whole surface of the barrier body or just part of the barrier body. Some of the projections (e.g., 336 of FIG. 6) may not be formed from the second material but may be another material for delivering a medicine or other material into the area during the healing process. In addition, while single substrate layers of material are shown, many variations are possible. For example, a flexible support or backing layer may be added (see, e.g., layer 642 below in FIG. 9). Further still, the materials may be a first thread material and a second thread material that are woven or non-woven into the barrier member.

In an alternative embodiment, the barrier body 314 may be formed with a single material and the thickness of the material may be varied. In this way, for example, the projections 336 may be formed by increasing the thickness in portions of the barrier body 314. In this embodiment, the material absorption rate for the material is a constant, but the effective absorption terms for various portions of the barrier body 314 will vary as a function of the thickness. The thicker portions will take longer to absorb than the thinner portions. Thus, a barrier member may be formed from a material with a first plurality of material portions having a first thickness ($t_1$) and a second plurality of material portions having a second thickness ($t_2$). The first thickness ($t_1$) is greater than the second thickness ($t_2$). With this arrangement, the barrier member has an effective bio-absorption term for the first plurality of material portions that is greater than an effective bio-absorption term for the second plurality of material portions.

Figure 7:
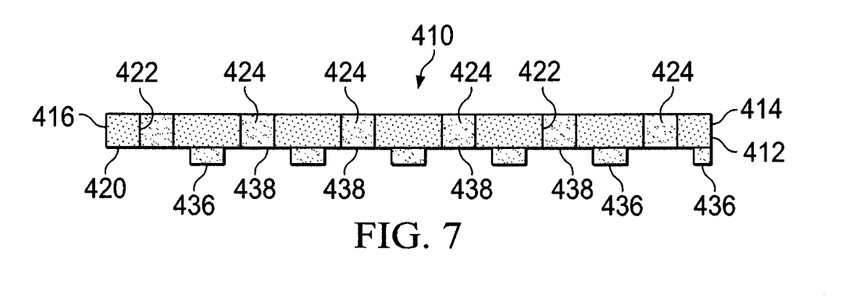
FIG. 7 is a schematic cross-section of another illustrative reduced-pressure manifold.

Referring now primarily to FIG. 7, an illustrative reduced-pressure manifold 410 is presented that is analogous in many respects to the reduced-pressure manifold 310 of FIG. 6. The reduced-pressure manifold 410 has a barrier member 412 with a barrier body 414. The barrier body 414 is formed from a first material 416 and has a plurality of apertures 422. A second material 424 is disposed in the apertures 422. The reduced-pressure manifold 410 is also formed with a plurality of projections 436 and concomitant flow channels 438 between the projections 436. The projections 436 are made by extruding, attaching, or otherwise forming the projections 436 on a second (tissue-facing) surface 420 of the barrier body 414. The projections 436 may take various shapes, e.g., cylindrical, rectangular (in cross-section), trapezoidal (in cross-section), conical, spherical, hemispherical, cubed, etc., and may be made from the first material 416, second material 424, or another material.

Figure 8:
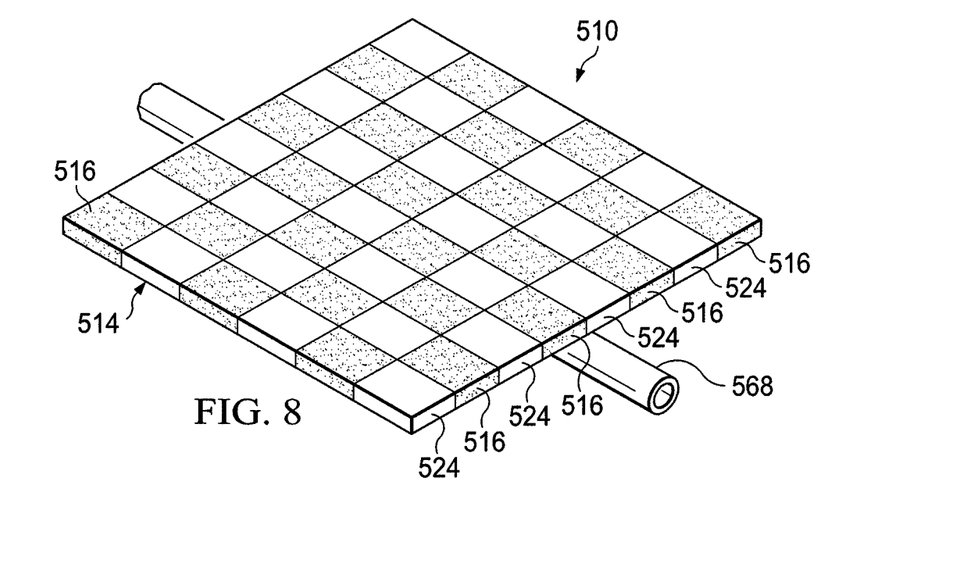
FIG. 8 is a schematic, perspective view of another illustrative embodiment of a reduced-pressure manifold.

Referring now to FIG. 8, another illustrative reduced-pressure manifold 510 is presented. The reduced-pressure manifold 510 is formed with two materials: first material units 516 and second material units 524. The first materials units 516 and second material units 524 may have the same or different absorptions rates or terms. In this embodiment, the material units 516 and 524 are abutting and formed as an integral barrier body 514. In one embodiment, the combined materials 516 and 524 provide adequate strength and mechanical properties for the treatment phase as reduced pressure is delivered through a delivery apparatus 568. One of the two materials is a quicker absorbing material and will absorb quicker than the other thereby allowing the treated tissue to chemically communicate with other tissues. The chemical communication may facilitate continued or expedited healing.

While shown with two materials, it should be understood that, amongst the many possible variations, a plurality of materials with different absorption terms (BA) cold be used to control the pattern and nature of the absorption of the reduced-pressure manifold 510. In addition, it should be noted that while consistent patterns of material are shown in this and the other embodiments, they may be varied as another control factor.

In the illustrative embodiment of FIG. 8, when the material with the shortest absorption term is absorbed, the remaining material will not be rigidly connected. There will, thus, be little or no continuing mechanical action. It may also be possible to have a drug-delivery material placed such that as the other materials are absorbed the drug-delivery material becomes exposed and begins to delivery medicine to the tissue site.

Figure 9:
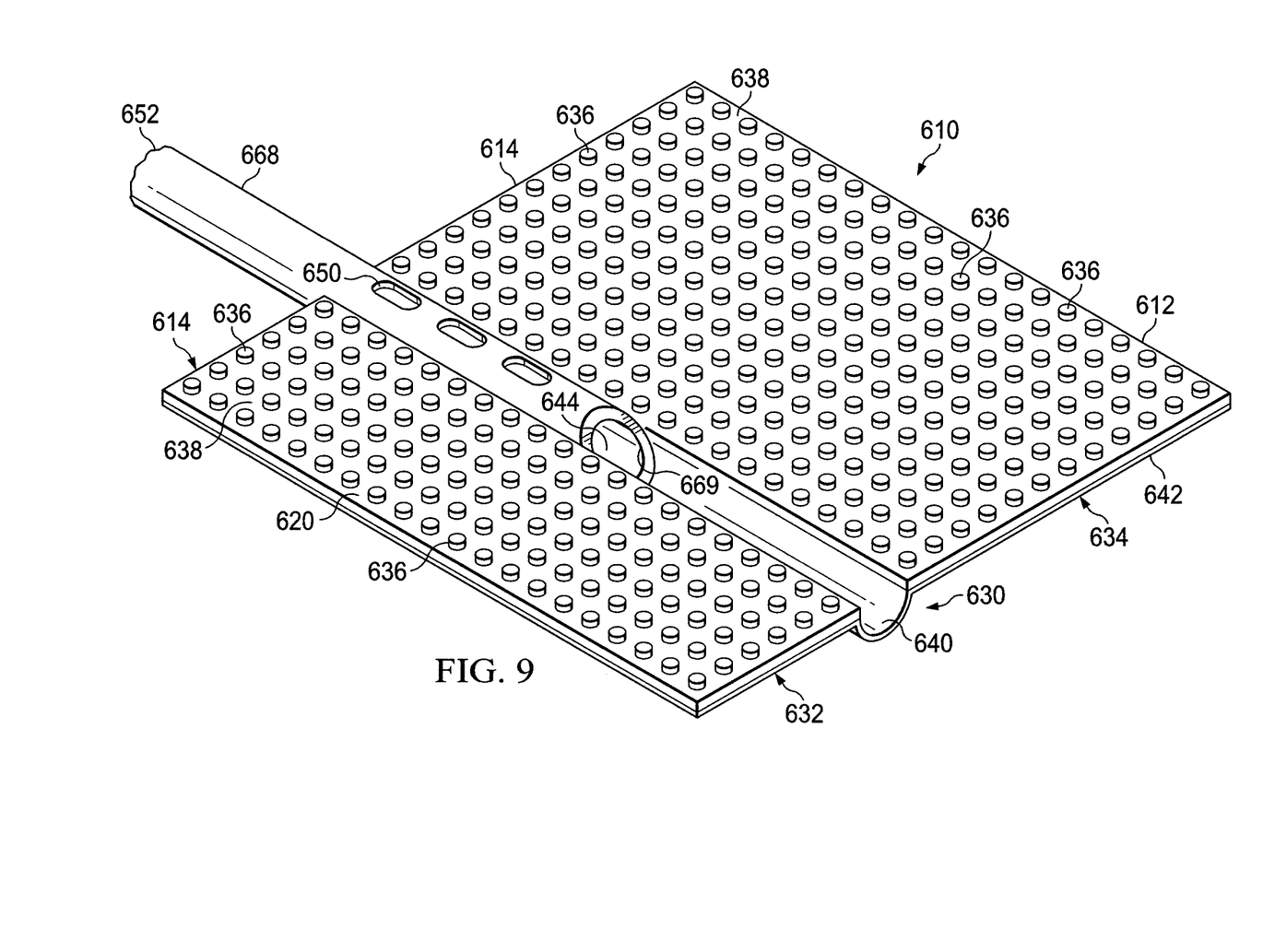
FIG. 9 is a schematic, perspective view of another illustrative embodiment of a reduced-pressure manifold.

Referring to FIG. 9, another illustrative embodiment of a reduced-pressure manifold 610, or manifold unit, adapted for use in a reduced-pressure delivery system, such as the reduced-pressure delivery system 100 of FIG. 1, is presented. The reduced-pressure manifold 610 includes a flexible barrier 612, which comprises a spine portion 630 and a first wing portion 632 and a second wing portion 634. The first wing portion 632 and the second wing portion 634 are positioned along opposite sides of the spine portion 630. The spine portion 630 forms an arcuate channel 640 that may or may not extend the entire length of the reduced-pressure manifold 610. Although the spine portion 630 may be centrally located on the reduced-pressure manifold 610 such that the width of the first wing portion 632 and second wing portion 634 are equal, the spine portion 630 may also be offset as shown in FIG. 9. The extra width of the second wing portions 634 may be particularly useful if the reduced-pressure manifold 610 is being used in connection with bone regeneration or healing and the wider reduced-pressure manifold 610 is to be wrapped around any fixation hardware attached to the bone. The thickness of the reduced-pressure manifold 610 may be less in the arcuate channel 640 than that in the wing portions 632, 634.

The reduced-pressure manifold 610 may further include materials that may serve as a scaffold for new cell-growth, or a scaffold material may be used in conjunction with the reduced-pressure manifold 610 to promote cell-growth. Suitable scaffold material may include, without limitation, calcium phosphate, collagen, PLA/PGA, coral hydroxy apatites, carbonates, or processed allograft materials. Preferably, the scaffold material will have a high void-fraction (i.e., a high content of air). Such scaffold materials may have relatively rapid or extremely slow rates of bio-absorption. For example, scaffold materials formed from collagen would have relatively rapid absorption rates while scaffold materials formed from calcium phosphate would have slow bio-absorption rates.

A flexible backing 642 may be affixed or attached to the flexible barrier 612 to provide additional strength and durability to the flexible barrier 612. The thickness of the flexible barrier 612 and the flexible backing 642 may be less in the arcuate channel 640 than that in the wing portions 632, 634. The reduced-pressure manifold 610 may include a first plurality of projections 636 extending from the first wing portion 632 and the second wing portion 634 on a second, tissue-face surface 620 of the reduced-pressure manifold 610. The projections 636 may be cylindrical, spherical, hemispherical, cubed, or any other shape, as long as at least some portion of each projection 636 is in a plane different than the plane associated with the side of the reduced-pressure manifold 610 to which the projections 636 are attached. In this regard, a particular projection 636 is not even required to have the same shape or size as other projections 636. The projections 636 may include a random mix of different shapes and sizes. Consequently, the distance by which each projection 636 extends from the manifold unit 610 may vary, but may also be uniform among the plurality of projections 636.

The placement of the projections 636 on the manifold unit 610 creates flow channels 638 between the projections. When the projections 638 are of uniform shape and size and are spaced uniformly on the reduced-pressure manifold 610, the flow channels 638 created between the projections 636 are similarly uniform. Variations in the size, shape, and spacing of the projections 636 may be used to alter the size and flow characteristics of the flow channels 638.

The flexible barrier 612, which may include backing 642, may be constructed of a bio-absorbable materials, as described above. The projections 636 may be formed as protrusions of a second material that fill apertures in the flexible barrier 612, or barrier body 614, like projections 336 in FIG. 6, and the second material may have a different bio-absorption term ($BA_2$) than the term of the flexible barrier body 614 ($BA_1$). For purposes of illustration, it is assumed here that the second material has a bio-absorption rate greater than the material of the flexible barrier 614, i.e., a shorter absorption term.

A reduced-pressure delivery member 668 is positioned within the arcuate channel 640 and is attached to the reduced-pressure manifold 610. The reduced-pressure delivery conduit 668 may be attached solely to the flexible barrier body 614 or to the flexible backing 642, or the delivery conduit 668 may be attached to both the flexible barrier 614 and the flexible backing 642. The reduced-pressure delivery conduit 668 includes a distal orifice 669 at a distal end of the conduit 668. The reduced-pressure delivery conduit 668 may be positioned such that the distal orifice 669 is located at any point along the arcuate channel 640, but the reduced-pressure delivery conduit 668 is shown positioned such that the distal orifice 669 is located approximately midway along the longitudinal length of the arcuate channel 640. The distal orifice 669 may be made elliptical or oval in shape by cutting the conduit 668 along a plane that is oriented less than ninety (90) degrees to the longitudinal axis of the reduced-pressure delivery conduit 668. While the orifice 669 may also be round, the elliptical shape of the orifice 669 increases fluid communication with the flow channels 638 formed between the projections 636.

In one illustrative embodiment, the reduced-pressure delivery conduit 668 may also include vent openings, or vent orifices 650 positioned along the reduced-pressure delivery conduit 668 as either an alternative to the distal orifice 669 or in addition to the distal orifice 669 to further increase fluid communication between the reduced-pressure delivery conduit 668 and the flow channels 638. The reduced-pressure delivery conduit 668 may be positioned along only a portion of the longitudinal length of the arcuate channel 640 as shown in FIG. 9, or alternatively may be positioned along the entire longitudinal length of the arcuate channel 640. If positioned such that the reduced-pressure delivery conduit 668 occupies the entire length of the arcuate channel 640, the distal orifice 669 may be capped such that all fluid communication between the conduit 668 and the flow channels 636 occurs through the vent orifices 650.

The reduced-pressure delivery conduit 668 further includes a proximal orifice 652 at a proximal end of the conduit 668. The proximal orifice 652 is configured to mate with a reduced-pressure supply conduit, such as the reduced-pressure conduit 170 of FIG. 1, and ultimately to be fluidly coupled to a reduced pressure source, such as reduced pressure source 160 in FIG. 1. The reduced-pressure delivery conduit 668 may include only a single lumen 644, but other embodiments of the reduced-pressure delivery conduit 668 may include multiple lumens such as a dual-lumen conduit. The dual-lumen conduit may be used to provide separate paths of fluid communication between the proximal end of the reduced-pressure delivery conduit 668 and the flow channels 636. The second lumen may be used to introduce a fluid to the flow channels 636. The fluid may be filtered air or other gases, antibacterial agents, antiviral agents, cell-growth promotion agents, irrigation fluids, chemically active fluids, or any other fluid. If it is desired to introduce multiple fluids to the flow channels 636 through separate fluid communication paths, a reduced-pressure delivery conduit may be provided with more than two lumens. In some clinical situations, it may be desirable to introduce a fluid that can accelerate or retard the degradation (or absorption) of one or more of the degradable components, or materials, of the flexible barrier.

In operation of a system with manifold 610, reduced pressure is delivered to the tissue site through the reduced-pressure manifold 610 and is accomplished by placing the wing portions 632, 634 of the flexible barrier 612 adjacent the tissue site, which in this particular example involves wrapping the wing portions 632, 634 around a void defect in the bone tissue site, e.g., bone fracture 106 of FIG. 1. In such a configuration, the reduced-pressure manifold 610 isolates the bone tissue site from surrounding soft tissue. Once treatment is completed, the reduced-pressure delivery conduit 668 may be removed and the reduced-pressure manifold 610 may be left in place is absorb. In one embodiment, the projections 636 are absorbed more quickly than the flexible barrier body 614, thereby permitting contact and chemical communication between the bone tissue site and the surrounding soft tissue much sooner than would otherwise occur.

Figure 10:
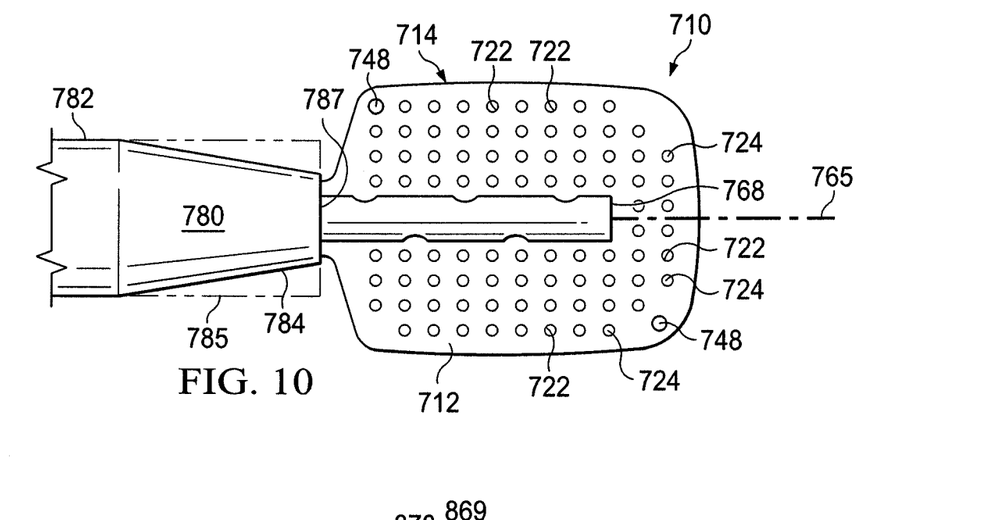
FIG. 10 is a schematic, bottom (tissue side) view of an illustrative embodiment of a reduced-pressure manifold and insertion device.

Referring now FIG. 10, a reduced-pressure manifold 710 and a manifold insertion device 780 for use with a system for providing reduced pressure to a treatment site on a patient are presented. The tissue site might include bone tissue adjacent to a fracture on a bone of the patient. The manifold insertion device 780 may include a delivery member 782 inserted through the patient's skin and any soft tissue surrounding the tissue site, e.g., bone. As previously discussed, the tissue site may also include any other type of tissue, including without limitation adipose tissue, muscle tissue, neural tissue, dermal tissue, vascular tissue, connective tissue, cartilage, tendons, or ligaments.

The delivery member 782 may include a tapered distal end 784 to ease insertion through the patient's skin and soft tissue. The tapered distal end 784 may further be configured to flex radially outward to an open position such that the inner diameter of the distal end 784 would be substantially the same as or greater than the inner diameter at other portions of the tube 782. The open position of the distal end 784 is schematically illustrated in FIG. 10 by broken lines 785.

The manifold delivery member 782 further includes a passageway 787 in which a flexible barrier 712, or reduced-pressure barrier, is during insertion. The flexible barrier 712 is preferably rolled, folded, or otherwise compressed around a reduced-pressure delivery member 768 to reduce the cross-sectional area of the flexible barrier 712 within the passageway 787. The delivery member 768 may be a catheter or cannula and may include features such as a steering unit and a guide wire 765 that allow the manifold delivery tube 721 to be guided to the tissue site 713.

The flexible barrier 712 may be placed within the passageway 787 and guided to the tissue site following the placement of the distal end 784 of manifold delivery member 782 at the tissue site. Alternatively, the flexible barrier 712 may be pre-positioned within the passageway 787 prior to the manifold delivery member 782 being inserted into the patient. If the reduced-pressure delivery member 768 is to be pushed through the passageway 787, a biocompatible lubricant may be used to reduce friction between the reduced pressure delivery member 768 and the manifold delivery member 782.

When the distal end 784 has been positioned at the tissue site and the reduced-pressure delivery member 768 has been delivered to the distal end 784, the flexible barrier 712 and reduced-pressure delivery member 768 are then pushed further toward the distal end 784, causing the distal end 784 to expand radially outward into the open position. The flexible barrier 712 is pushed out of the manifold delivery member 782, preferably into a void or space adjacent the tissue site. The void or space is typically formed by dissection of soft tissue, which may be accomplished by percutaneous devices. In some cases, the tissue site may be located at a wound site, and a void may be naturally present due to the anatomy of the wound. In other instances, the void may be created by balloon dissection, sharp dissection, blunt dissection, hydrodissection, pneumatic dissection, ultrasonic dissection, electrocautery dissection, laser dissection, or any other suitable dissection technique.

When the flexible barrier 712 enters the void adjacent the tissue site, the flexible barrier 712 either unrolls, unfolds, or decompresses from an initial insertion to an activation position as shown in FIG. 10. Although not required, the flexible barrier 712 may be subjected to a reduced pressure supplied through the reduced pressure delivery tube 768 to compress the flexible barrier 712. The unfolding of the flexible barrier 712 may be accomplished by either relaxing the reduced pressure supplied through the reduced pressure delivery tube 768 or by supplying a positive pressure through the reduced pressure delivery tube 768 to assist the unrolling process so that the flexible barrier 712 is an activation position. Final placement and manipulation of the flexible barrier 712 may be accomplished by using endoscopy, ultrasound, fluoroscopy, auscultation, palpation, or any other suitable localization technique. Following placement of the flexible barrier 712 and reduced-pressure delivery member 768, the manifold delivery tube 782 is preferably removed from the patient, but the reduced-pressure delivery tube 768 associated with the flexible barrier 712 remains in situ to allow percutaneous application of reduced pressure to the tissue site. The flexible barrier 712 may be made of at least two different materials having different bio-absorption terms.

The flexible barrier 712 may be formed with a barrier body 714 of a first material, which has a first bio-absorption term ($BA_1$), and formed with a plurality of apertures 722. The apertures 722 may be filled with a second material 724, which has a second bio-absorption term ($BA_2$), or even additional materials. The first bio-absorption term may be greater than the second. Radio-opaque members 748 may be included to help confirm placement of the manifold 710.

Once reduced-pressure treatment is completed, reduced-pressure delivery member 768 may be removed and manifold 710 left to be absorbed. If the second bio-absorption term is selected to be less than the bio-absorption term of the first material, the barrier body 714 will next have a plurality of open apertures 722 allowing chemical communication between the treated tissue site and other tissue.

Figure 11A:
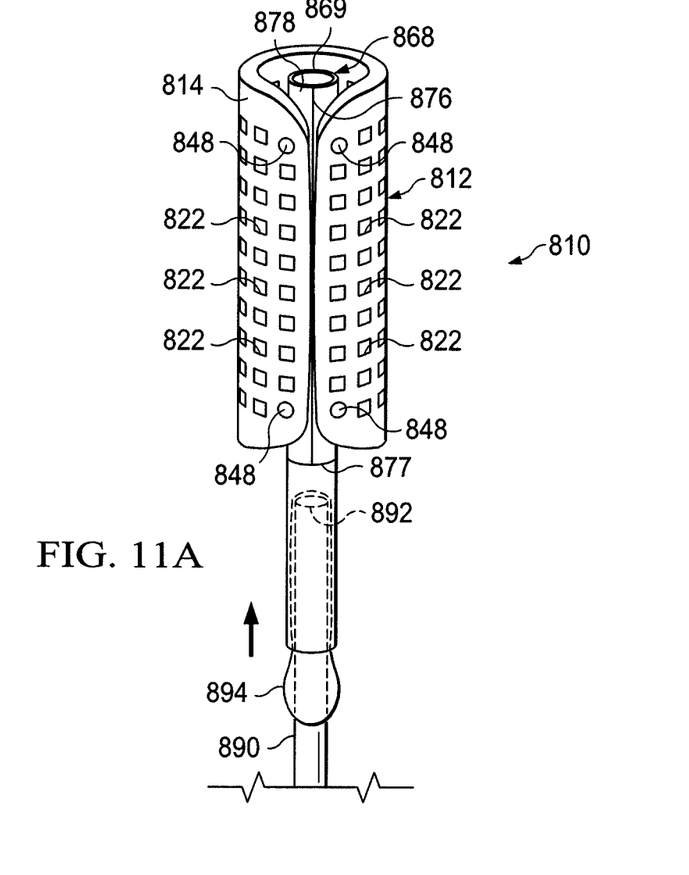
FIG. 11A is a schematic, bottom (tissue side) view of an illustrative embodiment of a reduced-pressure manifold for percutaneous insertion.
Figure 11B:
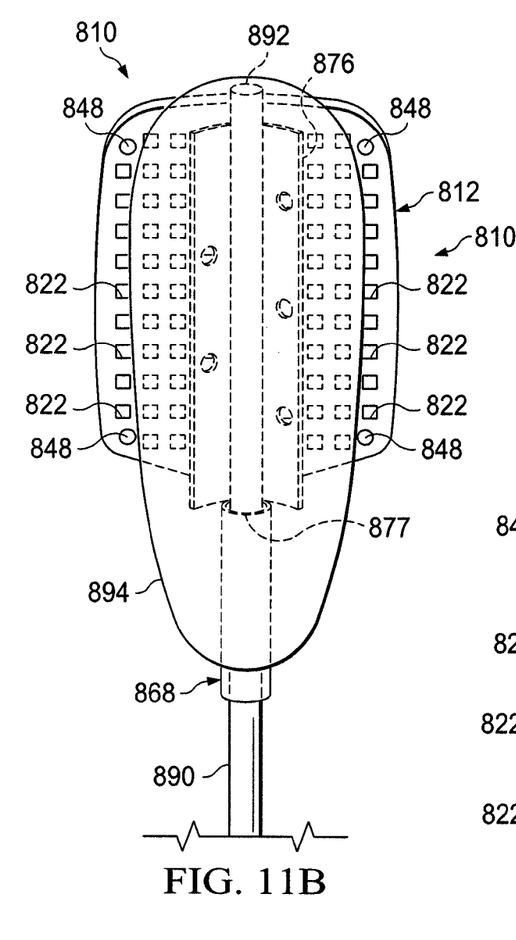
FIG. 11B is a schematic, bottom (tissue side) view of the illustrative embodiment of a reduced-pressure manifold of FIG. 11A showing activation.
Figure 11C:
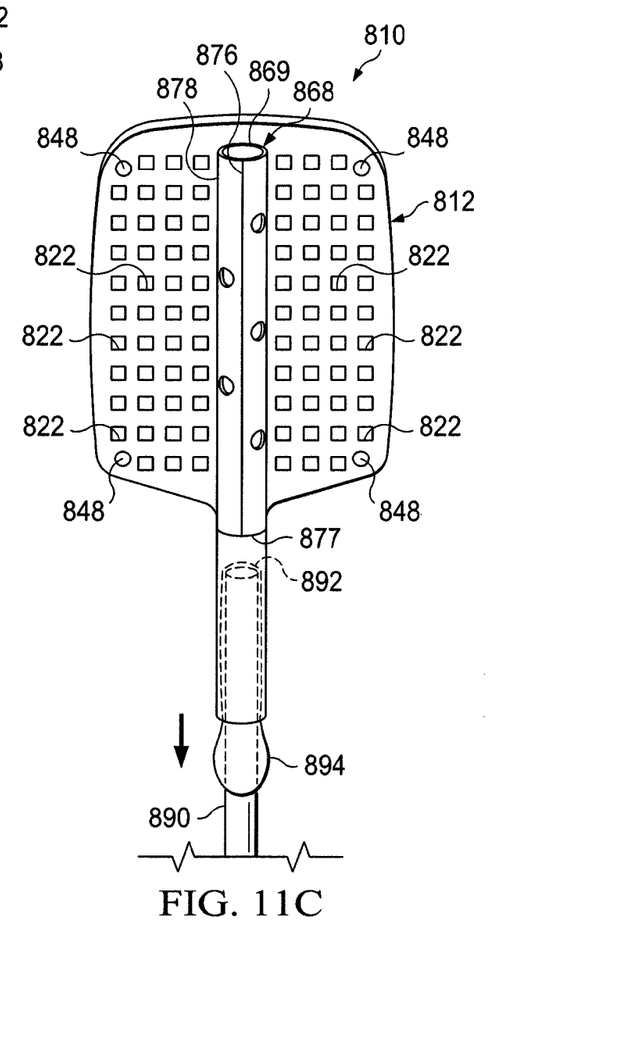
FIG. 11C is a schematic, bottom (tissue side) view of the reduced-pressure manifold of FIG. 11A showing the manifold in an activated position.

Referring now to FIGS. 11A-C, another reduced-pressure manifold 810 is presented. In FIG. 11A, the reduced-pressure manifold 810 is shown configured for percutaneously insertion (insertion position). FIG. 11B shows the reduced-pressure manifold 810 in the process of going from an insertion position to an activation position, Finally, the reduced-pressure manifold 810 is shown in an activation position in FIG. 11C just as the insertion device, e.g., sheath has been removed.

Referring primarily to FIG. 11A, a reduced-pressure delivery member 868 has been inserted, such as by using a dilator and then a sheath (not shown), into a patient and brought to a place proximate the tissue to be treated, e.g., bone defect 106 of FIG. 1. Any reduced pressure held on the delivery member 868 is released or a positive-pressure is applied on the delivery member 868 to cause a flexible barrier member 812 to at least partially unroll and begin to go from an insertion position to an activation position. The delivery member 868 may have a slit or small, longitudinal opening 876 formed on a first side portion 878. The slit 876 may allow the delivery member 868 to open when placed under positive-pressure as will be explained. The flexible barrier 812 may be formed with at least two materials. A barrier body 814 is formed from a first material and is formed with apertures 822 filled with a second material. Radio-opaque members 848 may be added at known locations, e.g. corners, to allow the placement of the manifold 810 to be verified and controlled.

A positive-pressure member or tube 890 having a distal end 892 is shown entering the reduced-pressure delivery member 868 in FIG. 11A. The positive-pressure member 890 has a flexible impermeable membrane 894, such a balloon, coupled to the distal end 892. The flexible impermeable membrane may be pushed through delivery member 868 until near the distal end 869. Once near the distal end 869, positive-pressure may be delivered through positive-pressure delivery member 868 to cause the flexible impermeable membrane 894 to inflate and thereby push outward the portion of delivery member 868 having slit 876. The portion of delivery member 868 and going from a lateral slit 877 to the distal end 869 changes from an insertion position to an activation position as shown in FIG. 11B. The activation position urges the flexible barrier member 812 into its activation position used for treatment as shown in FIG. 11C. The membrane 894 is then deflated and the positive-pressure member 890 is removed as is shown in FIG. 11C.

After the flexible barrier 812 is in place and the positive-pressure member 890 is removed, reduced pressure may be supplied through delivery member 868 to provide reduced pressure treatment to the tissue site. Once treatment is completed, it may desirable for the treated tissue to again chemically communicate with other tissue. The second material in apertures 822 may absorb before the barrier body 814 and thereby form open apertures that allow such chemical communication.

Although the present invention and its advantages have been disclosed in the context of certain illustrative, non-limiting embodiments, it should be understood that various changes, substitutions, permutations, and alterations can be made without departing from the scope of the invention as defined by the appended claims. It will be appreciated that any feature that is described in a connection to any one embodiment may also be applicable to any other embodiment.

I claim:

1. A reduced-pressure delivery manifold for percutaneous delivery of reduced pressure to a tissue site, comprising:
   a flexible barrier member formed from a first material having a first bio-absorption term and having a first surface and a second, tissue-facing surface including a plurality of projections extending from the tissue-facing surface, the projections being formed from a second material having second bio-absorption term wherein the first bio-absorption term is greater than the second bio-absorption term, the first material adapted to stabilize the tissue site;
   a barrier body having a different bioabsorption term than the first and second bioabsorption terms between the first surface and the second, tissue-facing surface of the flexible barrier member, wherein the barrier body comprises apertures at least partially filled by the projections extending into the aperture; and
   a reduced-pressure delivery member coupled to the flexible barrier member for delivering reduced pressure to the tissue-facing surface of the flexible barrier member when disposed adjacent the tissue site and having a distal end with at least one delivery aperture for delivering reduced pressure to the tissue site and a proximal end for receiving reduced pressure from a source a reduced pressure.

2. The reduced-pressure delivery manifold of claim 1, wherein the flexible barrier member comprises a spine portion, a first wing portion, and a second wing portion, the first wing portion positioned opposite the second wing portion along the spine portion.

3. The reduced-pressure delivery manifold of claim 1 wherein reduced-pressure manifold comprises a barrier body having a first plurality of a barrier units formed from the first material and a second plurality of barrier units formed from the second material.

4. The reduced-pressure delivery manifold of claim 1 wherein reduced-pressure manifold comprises a barrier body having a first plurality of a barrier units formed from the first material and a second plurality of barrier units formed from the second material; and wherein the first plurality of barrier units and the second plurality of barrier units laterally abut one another.

5. The reduced-pressure delivery manifold of claim 2, wherein the spine portion forms in arcuate channel extending a portion of the length of the reduced-pressure manifold.

6. The reduced-pressure delivery manifold of claim 2, wherein the spine portion is offset from the center of the flexible barrier member wherein the width of the first wing portion is greater than the width of the second wing portion.

7. The reduced-pressure delivery manifold of claim 1, further comprising scaffold material to support new cell growth.

8. The reduced-pressure delivery manifold of claim 7, wherein the scaffold material has a high void-fraction.

9. The reduced-pressure delivery manifold of claim 1, further comprising a flexible backing attached to the first surface of the flexible barrier member.

10. The reduced-pressure delivery manifold of claim 1, wherein the distal end of the reduced-pressure delivery member is disposed approximately midway along the longitudinal length of the flexible barrier member.

11. The reduced-pressure delivery manifold of claim 1, wherein the reduced-pressure delivery member further comprises vent orifices disposed along the longitudinal length thereof between the distal end and the proximal end.

12. The reduced-pressure delivery manifold of claim 11, wherein the distal end of the reduced-pressure delivery member is closed.

13. The reduced-pressure delivery manifold of claim 1, further comprising a reduced pressure conduit fluidly coupled to the proximal end of the reduced pressure delivery member for receiving reduced pressure from the source reduced pressure.

14. The reduced-pressure delivery manifold of claim 13, wherein the reduced pressure conduit includes at least two lumens adapted to provide separate paths of fluid communication to the proximal end of the reduced pressure delivery member.

15. The reduced-pressure delivery manifold of claim 14, wherein one of the at least two lumens adapted to provide a liquid fluid to the proximal end of the reduced pressure delivery member.

* * * * *